United States Patent [19]
Broude et al.

[11] Patent Number: 5,625,193
[45] Date of Patent: Apr. 29, 1997

[54] OPTICAL INSPECTION SYSTEM AND METHOD FOR DETECTING FLAWS ON A DIFFRACTIVE SURFACE

[75] Inventors: Sergey V. Broude, Newton Centre; Nicholas Allen, Bedford; Abdu Boudour, West Newton; Eric Chase, Carlisle; Carl Johnson, Tewksbury; Pascal Miller, North Chelmsford; Jay Ormsby, Salem, all of Mass.

[73] Assignee: QC Optics, Inc., Burlington, Mass.

[21] Appl. No.: 500,191

[22] Filed: Jul. 10, 1995

[51] Int. Cl.$^6$ .................................................. G01N 21/47
[52] U.S. Cl. ................ 250/372; 250/360.1; 250/559.18
[58] Field of Search ........................... 250/372, 358.1, 250/360.1, 559.16, 559.18, 359.1

[56] References Cited

U.S. PATENT DOCUMENTS

| | | |
|---|---|---|
| 4,655,592 | 4/1987 | Allemand ........................... 250/559.16 |
| 4,794,264 | 12/1988 | Quackenbos et al. . |
| 4,794,265 | 12/1988 | Quackenbos et al. . |
| 4,943,734 | 7/1990 | Johnson et al. . |
| 5,389,794 | 2/1995 | Allen et al. . |
| 5,493,123 | 2/1996 | Knollenberg et al. ............... 250/358.1 |

*Primary Examiner*—Carolyn E. Fields
*Attorney, Agent, or Firm*—Iandiorio & Teska

[57] ABSTRACT

An improved optical inspection system for detecting flaws on a diffractive surface containing surface patterns includes: an ultraviolet illumination means for illuminating a region on the diffractive surface to generate a scattered intensity distribution in response to either a flaw or a surface pattern; means for detecting the intensity level of the scattered intensity distribution at a plurality of locations about the diffractive surface; means for establishing a minimum detected intensity level; means, responsive to the minimum detected intensity level, for indicating the absence of a flaw on the illuminated region of the diffractive surface when the minimum detected intensity level is below a threshold intensity level and for indicating the presence of a flaw on the illuminated region of the diffractive surface when the minimum detected intensity level exceeds the threshold intensity level; and means for moving the diffractive surface to generate a scan pattern on the diffractive surface to inspect the entire surface.

41 Claims, 9 Drawing Sheets

OPTICAL INSPECTION SYSTEM AND METHOD FOR DETECTING FLAWS ON A DIFFRACTIVE SURFACE

FIELD OF INVENTION

This invention relates to an improved optical inspection system and method for detecting flaws on a diffractive surface with pattern features, and more particularly to such a system which differentiates between light scattered by a pattern on the surface and light scattered by a flaw.

BACKGROUND OF INVENTION

Detection of flaws such as particles, holes, bumps, pits or fingerprints on a surface having diffractive features, such as on a semiconductor wafer, a photolithographic mask used in modern semi-conductor lithography, or any other defect on a patterned surface hereinafter generically referred to as a "plate", is critical to maintaining a high level of quality control.

A system which accomplishes this function is disclosed in U.S. Pat. No. 4,943,734 assigned to the same assignee as the instant application, which is incorporated herein by reference in its entirety. That system utilizes a laser which provides a beam of visible, blue laser light (at the wavelength of 488 nm) that is scanned across the entire surface of the plate. The angular intensity distribution sensed by an array of detectors in response to the illumination at each point on the plate surface is used to determine the location and size of flaws on the plate surface. This system has several shortcomings, however.

With the decreasing size of elements in semiconductor devices, for example, it has become increasingly more important to detect smaller flaws on plates under inspection. The wavelength of the light beam used to probe the surface under inspection is one of the parameters that limits the size of the smallest flaws which can be detected. This is because the optical scattering cross-section decreases sharply as the wavelength increases (for flaws that are smaller in size compared to the beam wavelength). Thus, the wavelength of the laser beam limits the smallest size particle which the system is capable of detecting. Additionally, the wavelength of the laser beam limits the size of the beam spot that can be projected onto the surface under inspection because as the wavelength of the laser beam increases so does the size of the beam spot that can be focussed onto the surface and therefore the optical power density on the surface decreases. A larger beam spot results in decreased sensitivity, as a smaller portion of the beam is affected by flaws on the surface.

Because the system of U.S. Pat. No. 4,943,734 uses a scanned beam, it is not possible to reduce the beam size without prohibitively increasing the cost of both the scanning and detection optics. Thus the sensitivity and resolution of this system are limited by the 488 nm wavelength of the laser beam. This is because this system utilizes transmissive optics to focus the beam onto the surface. In order to focus a smaller beam onto the surface, larger lenses must be used which require larger lens holders. Thus, to decrease the beam spot size large, bulky and more expensive optics are required. Such optics are more difficult to scan.

SUMMARY OF INVENTION

It is therefore an object of this invention to provide an improved optical inspection system for detecting flaws on a diffractive surface.

It is a further object of this invention to provide such an improved optical inspection system which can detect smaller flaws than conventional optical inspection systems.

It is a further object of this invention to provide such an improved optical inspection system which has improved flaw resolution capabilities.

It is a further object of this invention to provide such an improved optical inspection system which has increased sensitivity.

It is a further object of this invention to provide such an improved optical inspection system which utilizes less complex and less expensive optics.

It is a further object of this invention to provide such an improved optical inspection system which utilizes strategically placed stationary detectors to optimize the sensitivity of the system.

It is a further object of this invention to provide such an improved optical inspection system which automatically discards unnecessary inspection dam relating to the pellicle frame.

This invention results from the realization that an improved optical inspection system and method for detecting flaws on a diffractive surface having greater sensitivity and increased resolution capabilities can be achieved by illuminating with an ultraviolet laser a spot of decreased size and a shorter wavelength on the surface, detecting the illumination scattered from the surface and determining the minimum intensity level detected to determine the location and size of flaws on the surface and from the further realization that the need for bulky, complicated and expensive optics can be avoided by using a stationary beam with stationary illumination and detection means and rotating and/or translating the surface so that the entire surface may be inspected.

This invention results from the further realization that overloading of system memory can be prevented by automatically discarding unnecessary inspection data to the pellicle frame and areas outside of the pellicle frame.

This invention features an improved optical inspection system for detecting flaws on a diffractive surface containing surface patterns. The system includes an ultraviolet illumination means for illuminating a region on the diffractive surface to generate a scattered intensity distribution in response to either a flaw or a surface pattern. There are means for detecting the intensity level of the scattered intensity distribution at a plurality of locations about the diffractive surface and means, responsive to the means for detecting for establishing a minimum detected intensity level. There are means, responsive to the minimum detected intensity level, for indicating the absence of a flaw on the illuminated region of the diffractive surface when the minimum detected intensity level is below a threshold intensity level and for indicating the presence of a flaw on the illuminated region of the diffractive surface when the minimum detected intensity level exceeds the threshold intensity level. There are means for moving the diffractive surface to generate a scan pattern on the diffractive surface to inspect the entire surface.

In a preferred embodiment the diffractive surface may be a photolithographic mask. The ultraviolet illumination means may include an ultraviolet laser which provides an ultraviolet laser beam for illuminating the diffractive surface. The ultraviolet laser may be a stationary ultraviolet laser. The ultraviolet laser may project an elliptical beam spot on the diffractive surface. The ultraviolet laser beam may impinge on the diffractive surface at an angle of approximately 60° from normal to the surface. The means for illuminating may include reflective means for directing and focusing the illumination on the diffractive surface. The reflective means may include a mirror and the mirror may be an off-axis parabolic mirror. The means for detecting may include a first detector at a first location proximate the diffractive surface for detecting the intensity level of the scattered intensity distribution at the first location and a second detector at a second location proximate the diffractive surface for detecting the intensity level of the scattered intensity distribution at the second location. The means for detecting may be positioned at locations about the diffractive surface where the intensity level of the scattered intensity distribution from the surface pattern is expected to be below the threshold intensity level. The means for moving may include means for rotating and translating the diffractive surface to establish a spiral trace including a plurality of revolutions of the ultraviolet laser beam on the diffractive surface. The beam width may be at least as large as the beam trace pitch to ensure inspection of the regions between revolution of the trace. The beam trace pitch may be no greater than approximately 3 micrometers. There may further be included means, responsive to the minimum detected intensity level, for determining flaw size. The means for moving may include encoder means for determining the position of the illuminated region on the diffractive surface. There may further be included means, responsive to the means for indicating and determining the position of the illuminated region, for storing the locations of the flaws detected. There may further be included means, responsive to the means for determining flaw size and the means for determining the position of the illuminated region on the surface, for storing the location and size of the flaws detected. There may further be included means for displaying the locations of the flaws detected. There may further be included means for positioning the diffractive surface in a first position with respect to the ultraviolet illumination means for conducting a first inspection of the diffractive surface and for positioning the diffractive surface in a second position with respect to the ultraviolet illumination means for conducting a second inspection of the diffractive surface to insure full inspection of the surface. There may further be included means for determining the regions on the diffractive surface covered by a pellicle frame and the regions on the diffractive surface external of the pellicle frame. There may further be included means, responsive to the means for determining the regions on the diffractive surface covered by the pellicle frame and the regions on the diffractive surface external of the pellicle frame, for discarding information from the means for detecting at these regions.

This invention further features an improved optical inspection method for detecting flaws on a diffractive surface containing surface patterns. The method includes illuminating a region on the diffractive surface with ultraviolet illumination to generate a scattered intensity distribution in response to either a flaw or a surface pattern. The method includes detecting the intensity level of the scattered intensity distribution at a plurality of locations about the diffractive surface and establishing a minimum detected intensity level. The method further includes indicating the absence of a flaw on the illuminated region of the diffractive surface when the minimum detected intensity level is below a threshold level and the presence of a flaw on the illuminated region of the diffractive surface when the minimum detected intensity level exceeds the threshold intensity level. The method also includes moving the diffractive surface to generate a scan pattern on the diffractive surface to inspect the entire surface.

In a preferred embodiment the diffractive surface may be a photolithographic mask. The step of illuminating may include providing an ultraviolet laser beam to the diffractive surface and the ultraviolet laser beam may be a stationary ultraviolet laser beam. The step of providing an ultraviolet laser beam may include projecting an elliptical beam spot onto the diffractive surface. The step of providing an ultraviolet laser beam may include directing the ultraviolet laser beam to the surface at an angle of approximately 60° from normal to the surface. The step of detecting may include detecting the intensity level of the scattered intensity a first location proximate the diffractive surface and detecting the intensity level of the scattered intensity distribution at a second location proximate the diffractive surface. The step of detecting may include detecting the intensity level of the scattered intensity distribution at locations about the surface where the intensity level of the scattered intensity distribution from the surface pattern is expected to be below the threshold intensity level. The step of moving may include rotating and translating the diffractive surface to establish a spiral trace including a plurality of revolutions of the ultraviolet laser beam on the diffractive surface. The step of rotating and translating may include overlapping each revolution of the spiral trace with adjacent revolutions to insure inspection of the regions between each revolution. The step of rotating and translating may include spacing the revolutions no greater than approximately 3 micrometers apart. The method may further include determining flaw size. The step of moving may include determining the position of the illuminated region on the diffractive surface. The method may further include storing the location and sizes of the flaws detected. The method may further include displaying the locations of the flaws detected. The method may further include positioning the diffractive surface in a first position with respect to the ultraviolet illumination for conducting a first inspection of the diffractive surface and positioning the diffractive surface in a second position with respect to the ultraviolet illumination for conducting a second inspection of the diffractive surface to insure full inspection of the surface. The method may further include determining the regions on the diffractive surface covered by a pellicle frame and the regions on the diffractive surface external of the pellicle frame and the step of determining may include discarding detected intensity levels from these regions on the diffractive surface.

DISCLOSURE OF PREFERRED EMBODIMENT

Other objects, features and advantages will occur to those skilled in the art from the following description of a preferred embodiment and the accompanying drawings, in which.

Figure 1:
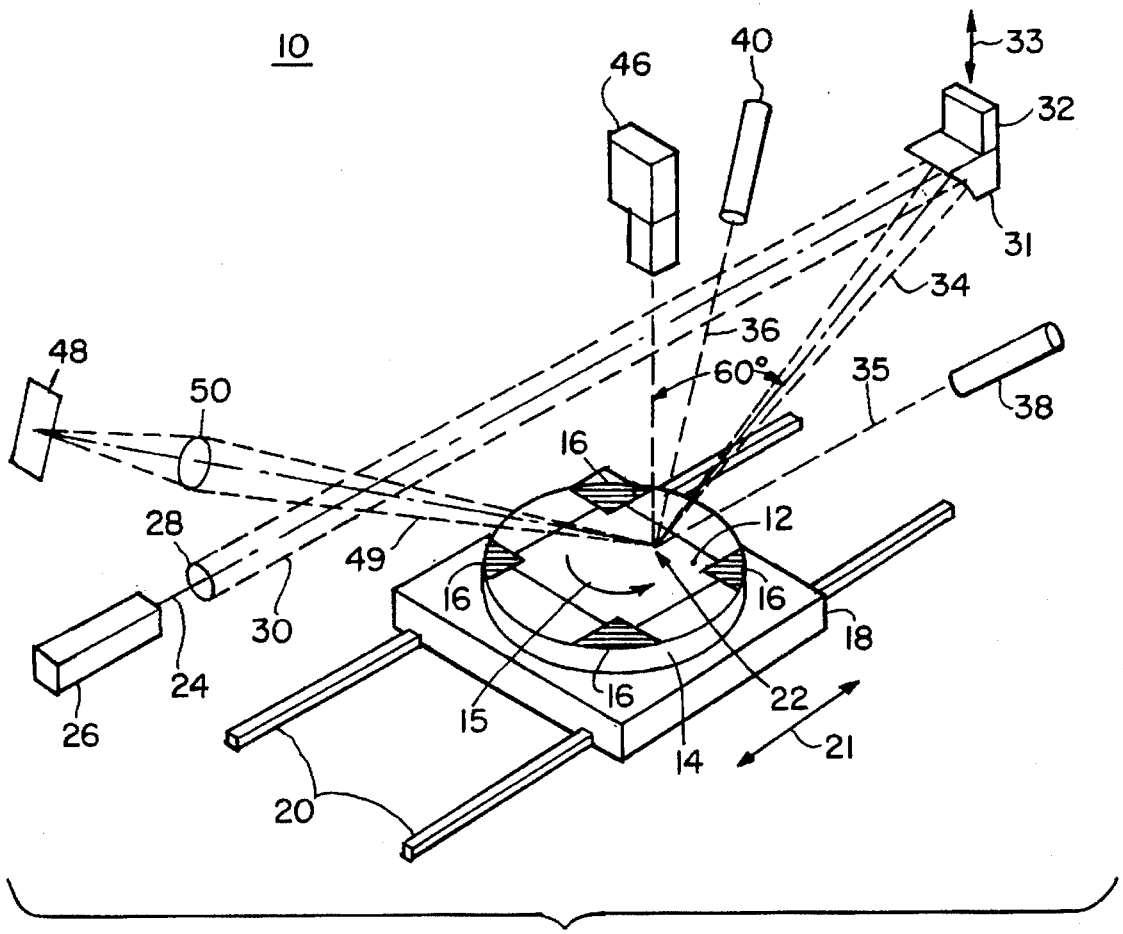
FIG. 1 is a three-dimensional view of the improved optical inspection system according to this invention.

There is shown in FIG. 1 an improved optical inspection system 10 according to this invention for detecting flaws on a diffractive surface such as the surface of plate 12. Plate 12 may be a photolithographic mask formed of a glass or quartz substrate which has on one of its surfaces a plurality of chrome patterns and on its other surface no patterns are generally formed. The plates are typically between 4 to 8 in. in width and 4 to 8 in. in length with a thickness of approximately 0.09 to 0.25 in.

Plate 12 is mounted on rotating plate holder 14 and secured thereon by securing and referencing means 16, such as reference surfaces or tabs at each corner of plate 12. Plate holder 14 is rotated in the direction of arrow 15 by a spindle (not visible in this figure) and is mounted upon translation stage 18 which translates in the direction indicated by arrows 21. Point of inspection 22 is illuminated with a stationary ultraviolet laser beam 24 which operates at two wavelengths, namely, 351 nm and 364 nm, generated by stationary laser source 26. Laser beam 24 passes through expander 28 which enlarges beam 24 into an expanded beam 30. Expanded beam 30 impinges upon the reflecting surface of off-axis parabolic mirror 31 which focuses the beam to a small spot on the surface of plate 12 and which is affixed to focusing actuator 32 which translates in the direction of arrows 33. Off-axis parabolic mirror 31 is positioned such that it forms a converging beam 34 focussed at inspection point 22 at an angle of approximately 60° from normal to the surface of plate 12. Plate holder 14 is rotated and translation stage 18 translates such that beam 34 at point 22 under inspection effectively traces a spiral path having a plurality of revolutions on the surface of plate 12. Plate holder 14 is typically vertically oriented to hold plate 12 in a vertical position to minimize the amount of contamination of the plate by airborne particles.

Light 35 and 36 scattered from point of inspection 22 on the surface of plate 12 as a result of a flaw or a regular surface pattern is received by detectors 38 and 40. Light incident upon a regular surface pattern is scattered to produce a number of substantial intensity levels separated by a number of very low intensity levels distributed fairly regularly about the pattern on the surface. Light incident upon a surface flaw, however, produces a fairly uniform high intensity scattering of light about the flaw. Thus, by placing detectors 38 and 40 in the regions where low levels of scattered light from patterns are expected, system 10, as described in detail below, can readily distinguish between flaws and surface patterns by determining the minimum detected intensity level from the detectors. If a very low level is detected at least by one of detectors 38 and 40, below a predetermined threshold, no flaw is present, while if levels above the threshold are detected by both detectors, a surface flaw is present. Although only two detectors are used in this configuration, this is not a necessary limitation of this invention, as any number of detectors greater than two could be used as long as at least some of them are located proximate the expected low scattering directions of the pattern scattering distribution.

Also included in system 10 is autofocus sensor head 46 which is used to sense plate position and to position accordingly off-axis parabolic focusing actuator 32 so that beam 34 is properly focused at point of inspection 22. Reflectometer detector 48 and reflectometer imaging lens 50 which receives beam 49 reflected from a pellicle (not shown in this figure) covering plate 12, are used to adjust the beam output from laser source 26 to compensate for signal attenuation caused by the pellicle, as described in detail below with regard to FIGS. 9 and 16.

Figure 2:
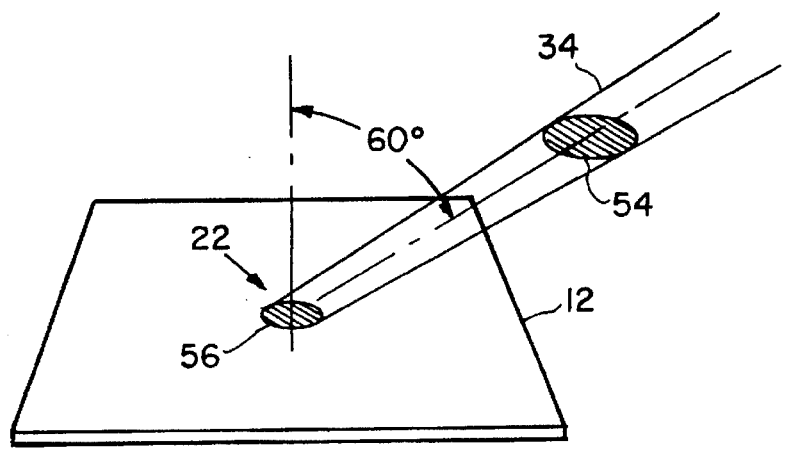
FIG. 2 is an enlarged three-dimensional view of the ultraviolet laser beam projected onto the surface of the plate under inspection shown in the system of FIG. 1.

Converging beam 34, FIG. 2, has an elliptical cross-section of approximately 2 by 5 microns as indicated at 54. When converging beam 34 is projected upon the surface of plate 12 an enlarged elliptical beam spot 56 is formed at point of inspection 22. Projected beam spot 56 on the surface of plate 12 is approximately 2 by 10 microns in size. Conventional inspection systems utilize a beam which produces a spot size between 15 and 50 microns. As discussed in the Background of Invention, a large spot size results in decreased resolution and sensitivity. Thus, by using an ultraviolet laser which produces a smaller beam spot, such as spot 56, the sensitivity and resolution of system 10 are significantly increased. Further, by using an ultraviolet laser having a shorter wavelength the sensitivity is additionally increased.

Figure 3:
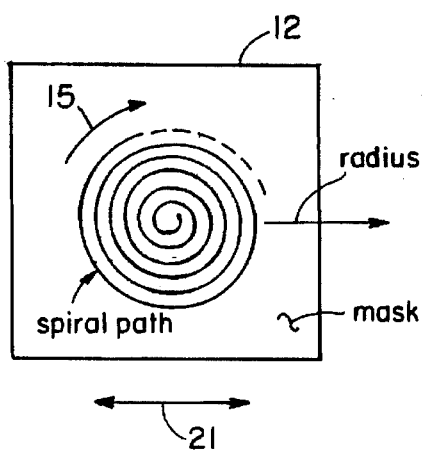
FIG. 3 is a schematic top plan view of a plate under inspection depicting the spiral path of the laser beam traced on the plate surface in the system of FIG. 1.
Figure 4:
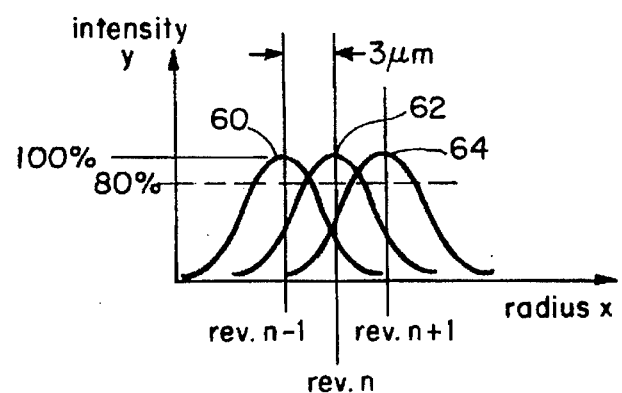
FIG. 4 is a plot of the intensity distribution vs. radius for three adjacent successive traces of the ultraviolet laser beam on the plate.

In order to inspect the entire surface of plate 12 with stationary converging beam 34, plate 12 is rotated in the direction of arrow 15 and translated in the direction of arrows 21 such that a spiral path 58, FIG. 3, of converging beam 34 is traced on the surface of plate 12. In order to insure adequate overlap of adjacent revolutions of spiral path 58, the trace pitch (distance from the center of each beam revolution to the center of its adjacent revolutions) of the spiral is set at approximately 3 μm. This is illustrated in FIG. 4 where the intensity profiles of three successive revolutions (N−1, N, N+1) of spiral trace 58 are shown as revolutions 60, 62 and 64, respectively. Revolutions 60, 62 and 64 represent a plot of the intensity of the trace which is indicated on the Y axis versus the radius which is indicated on the X axis. By selecting a 3 μm pitch (the centers of successive revolutions are spaced 3 μm apart) with a 2×10 micrometer beam, adequate overlap is obtained as shown at the 80% intensity level of the beam. It is known from the gaussian profile of converging beam 34 that at 80% intensity the beam width will be approximately 3.33 μm. Thus, by choosing a 3 μm pitch adequate overlap is insured and no portion of surface 12 between successive revolutions of spiral trace 58 is left uninspected.

Figure 6A:
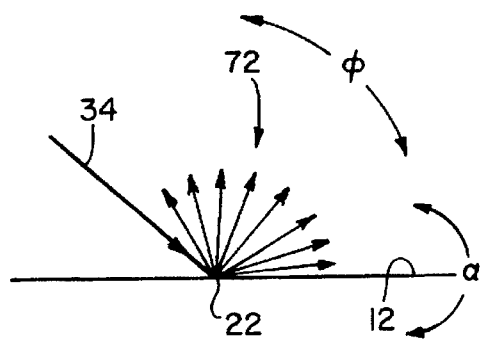
FIG. 6A is a schematic view of the scattered intensity distribution as a result of an ultraviolet laser beam impinging upon a particle.
Figure 6B:
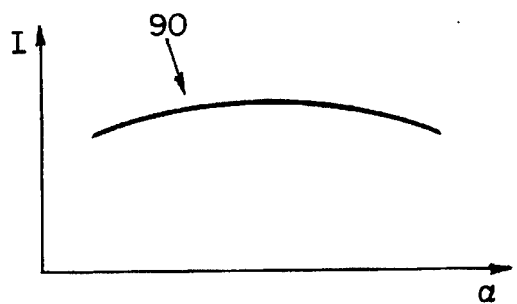
FIG. 6B is a plot of the intensity of the scattering distribution of FIG. 6A over the range of angles α about the point under inspection.
Figure 7:
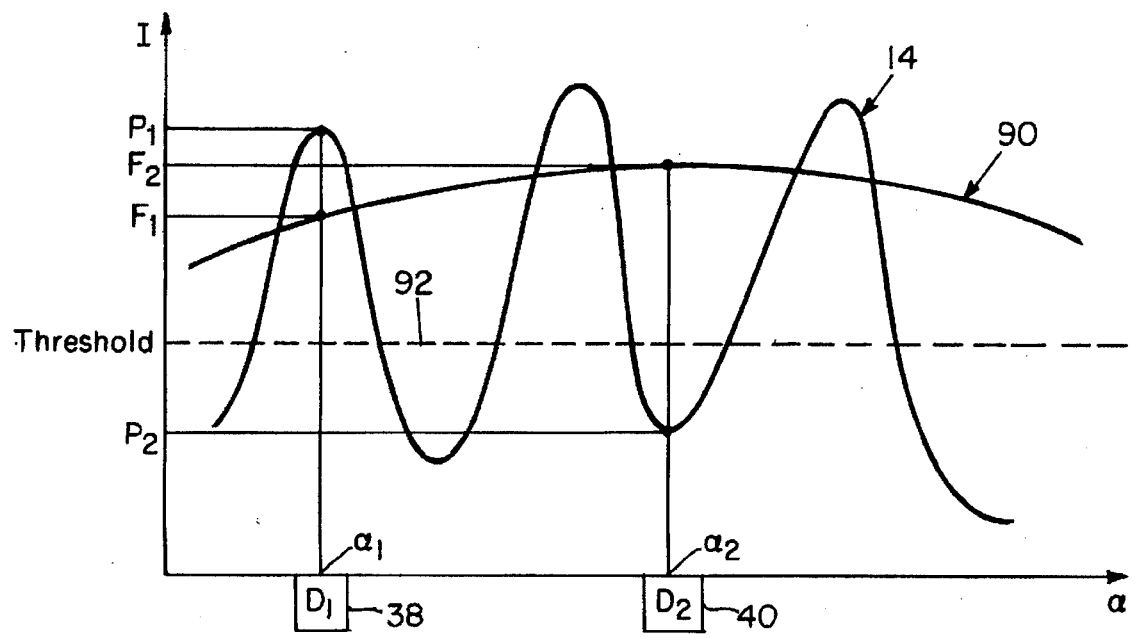
FIG. 7 is a plot which includes the angular intensity distributions depicted in FIGS. 5B and 6B superimposed.

The scattered light intensity distributions of FIGS. 5–7 illustrate that light scattered from regular surface patterns produce intensity distributions which have peaks of substantial magnitude, well defined, and separated by regions which are at or below the noise level. In contrast, light scattered from flaws produce a substantially uniform high intensity level with no low intervals.

Figure 5A:
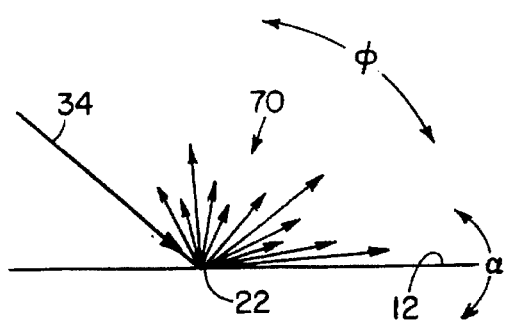
FIG. 5A is a schematic view of the scattered intensity distribution as a result of an ultraviolet laser beam impinging upon a surface pattern.

Scattered light distribution 70, FIG. 5A, results from converging laser beam 34 impinging upon a regular surface pattern at point of inspection 22. The distribution is not uniform over the range of angles ϕ above surface 12, but rather it has a number of varying intensity levels, some are at fairly high intensities while others are at much lower intensities. In contrast, as shown in FIG. 6A, scattered light distribution 72 which results from converging beam 34 impinging upon a flaw at point of inspection 22 on the surface of plate 12 produces a more uniform scattered light distribution over the range of angles ϕ. The scattered light from a flaw and a surface pattern over angles ϕ are distributed similarly over the range of angles α azimuthally about point of inspection 22. Thus, scattered light distributions 70 and 72 are actually three-dimensional semi-spherical scattered light distributions. Distribution 72 is approximately a uniform semi-spherical distribution while distribution 70 is a distribution with a number of peaks and low levels.

Figure 5B:
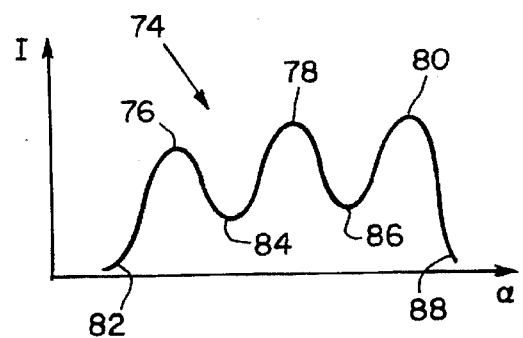
FIG. 5B is a plot of the intensity of the scattered intensity distribution of FIG. 5A over the range of angles $\alpha$ about the point under inspection.

The intensity levels of the light distributions scattered from both the regular surface pattern and flaw over a range of angles α about point of inspection 22 are shown in FIGS. 5B and 6B, respectively. In FIG. 5B the intensity response 74 of scattered light distribution 70 from a pattern is shown to include a number of peaks 76, 78 and 80 as well as a number of lower levels 82, 84, 86 and 88 over the range of angles α. In contrast, intensity response 90 of scattered light distribution 72 from a flaw about the range of angles α about point of inspection 22 is much more uniform. The intensity level is nearly equal over the range of angles in which light is detected.

Pattern intensity distribution 74 and flaw intensity distribution 90 are superimposed and the intensity levels detected by specifically placed detectors 38 ($D_1$) and 40 ($D_2$), FIG. 1, are shown in FIG. 7. This figure demonstrates how the optical inspection system of this invention differentiates between flaws and surface patterns. Detector 38 located at angle $\alpha_1$ receives a light intensity level $F_1$ when scattered light distribution 90 is generated because of the presence of a flaw on the surface of plate 12. Detector $D_2$ at angle $\alpha_2$ detects a light intensity $F_2$. The system according to this invention, as described below, determines the minimum detected intensity level, which in this case is $F_1$, and compares that level to threshold level 92. If the minimum detected intensity level from the detectors 38 and 40 exceed threshold level 92, a flaw is present at the point of inspection. From the level of intensity detected the approximate particle size can be determined: the greater the intensity the greater the flaw size. If, on the other hand, a regular surface pattern causes scattered light distribution 74, detector 38 $D_1$ at angle $\alpha_1$ detects intensity level $P_1$, while detector 40 $D_2$ at angle $\alpha_2$ detects level $P_2$. Intensity level $P_2$ is then determined to be the minimum detected intensity level and since this level is below threshold 92 the system indicates that a regular surface pattern has been detected at the point of inspection and that no flaw is present.

Regular surface patterns produce very similar scattered light distributions which have low intensity levels such as levels 82, 84, 86, 88, FIG. 6B, that regularly are present in known locations about the point of inspection on a surface. Thus, it is desirable to locate detectors 38 and 40 (and any additional detectors) at locations about the surface under inspection where low scattered light intensity levels from patterns are expected. Threshold level 92 is variable, however, it must always be set slightly higher than the minimum level expected to be detected from one of the detectors as a result of a surface pattern. Thus, this level limits the minimum size flaw that can be detected. Flaws which have an intensity response which is less than the lowest possible threshold 92 or lower than the lowest detected intensity level of pattern response 74 will not be detected as a flaw. The lower limit on this system is approximately 0.3 micron flaw detection.

Figure 8:
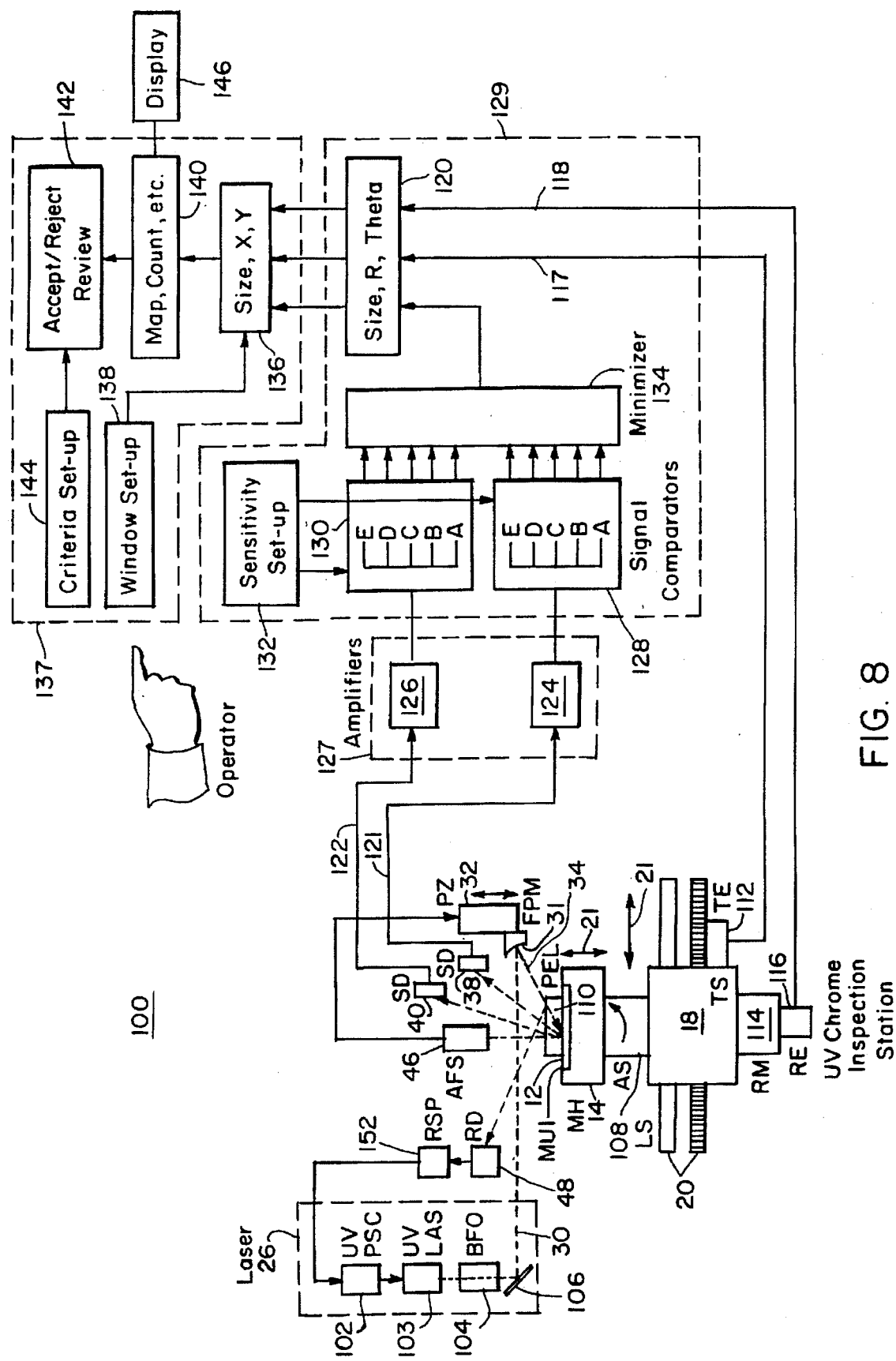
FIG. 8 is a schematic block diagram of an optical inspection station according to this invention.

There is shown in FIG. 8 optical inspection station 100 including optical inspection system 10, FIG. 1, and detection, mapping and particle size determination electronics. Station 100 includes laser source 26 having ultraviolet laser power supply and control 102 which drives ultraviolet laser 103. Ultraviolet laser 103 through beam forming optics 104 produces a laser beam 30 which is provided to mirror 106 to redirect laser beam 30 to off-axis parabolic mirror 31. Off-axis parabolic mirror 31 forms converging beam 34 which is focussed onto the surface of plate 12. Plate 12 is mounted within plate holder 104 which itself is mounted upon and rotated in the counter clockwise direction by rotation spindle 108. There is included a pellicle 110 which protects plate 12.

Pellicle 110, plate 12, plate holder 14 and rotation spindle 108 are all mounted on translation stage 18 which translates upon rails 20 in the direction of arrows 21. Translation encoder 112 tracks the precise radial position of point under inspection 22 on plate 12 from the starting point of the inspection. Rotation motor 114 drives rotation spindle 108, and rotation encoder 116 tracks the precise rotational (angular) position of plate 12 and hence the location of point under inspection 22 on the surface of plate 12. The translational and rotational signals are provided over lines 117 and 118, respectively, to polar coordinate particle detector 120. Also input to polar coordinate flaw detector 120 is a signal indicative of the size of the flaw detected or a zero level signal if a pattern or nothing is detected on the surface of plate 12. Thus, flaw detector 120 provides an output of the polar coordinates of a located flaw on surface 12 and the flaw size.

The location and size of a detected flaw is determined first by detecting the level of the scattered light distribution received by detectors 38 and 40 from the ultraviolet illumination of a point of inspection 22 on the surface of plate 12. Detectors 38 and 40 provide an electrical signal corresponding to the intensity of light detected over lines 121 and 122 to amplifiers 124 and 126, respectively, within analog signal processing circuit 127. The amplified signals are provided to two sets of signal comparators 128 and 130 within digital signal processing circuit 129. Comparators 128 and 130, which may be LT1016 circuits produced by Linear Technology, each output a digital word to minimizer 134, which may be a 20V8 circuit produced by Lattice Semiconductor. A comparator output signal equal to zero indicates that neither detector 38 nor 40 detected an intensity level which is above the threshold level. Signals that exceed the threshold level produce different digital words that correspond to the size of the signal and hence the size of the flaw detected. In this example only five different flaw sizes (A-E) are shown, however, a greater number of sizes could be used. Sensitivity set-up circuit 132 enables the adjustment of the levels A-E so that an operator can vary the sensitivity level for different applications. The digital words corresponding to the signals detected from comparators 128 and 130 are provided to minimizer 134 which outputs the minimum intensity level detected by detectors 38 and 40. If the digital output from minimizer 134 is equal to zero this indicates that a pattern (or nothing) was detected at that particular point on plate 12. A non-zero output indicates that a flaw is present and the data is provided to polar coordinate particle detector 120 which simultaneously receives the polar coordinates, R and Θ, of the location of the flaw detected from translational and rotational encoders 112 and 116, respectively. The flaw size and the polar coordinates are provided to cartesian conversion program 136 within computer control and data storage unit 137, which converts the polar coordinates R and Θ to cartesian coordinates X and Y and receives the flaw size signal. There is a window setup program 138 which enables the operator to input the size of the plate 12 and its quality area under inspection so that the proper cartesian coordinates X and Y can be determined, e.g. only the area within the pellicle frame.

The cartesian coordinates and flaw size are provided to flaw mapping program 140 which stores the location and size of each flaw detected. After the entire surface of plate 12 has been inspected and the location and size of each flaw on the surface of plate 12 has been stored by flaw mapping program 140, accept/reject program 142 makes a determination based on certain criteria provided by an operator-defined parameter list 144 whether or not to accept or reject the particular plate under inspection. For example, if the total number of flaws detected exceeds a predetermined number or if a predetermined number of certain size flaws is exceeded then the plate is rejected. Flaw mapping program 140 also provides the location and flaw size information to display 146, FIG. 9, which enables visual observation of the flaw locations on plate 12. Plate 12 having a number of flaws 148 is displayed. Also, the total flaw count on plate 12 as well as the count of each different flaw size is shown in display portion 150.

Also included in station 100 is reflectometer detector 48 which detects the specularly reflected light from the surface of pellicle 110 and provides a signal to reflectometer signal processing 152 which in turn provides a control signal to ultraviolet laser power supply and control 102. The signal from reflectometer signal processing 152 increases the ultraviolet laser power and control signal to ultraviolet laser 103 in order to increase the intensity of laser beam 30 output from laser source 26 to compensate for the light reflected from the surface of pellicle 110 which attenuates the input beam and the scattered light signal received by detectors 38 and 40. Or, sensitivity levels in detectors 38 and 40 are accordingly increased.

Figure 10:
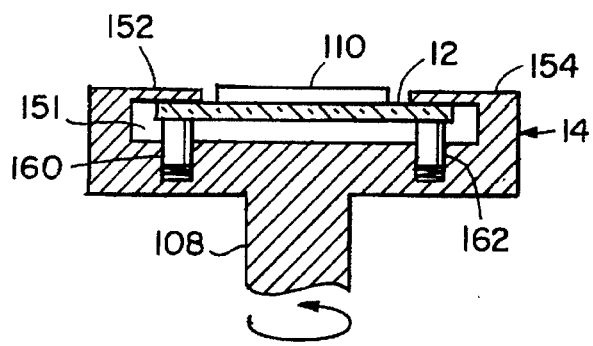
FIG. 10 is a schematic cross-sectional view of the plate holder and plate shown in the system of FIG. 1 according to this invention.
Figure 11:
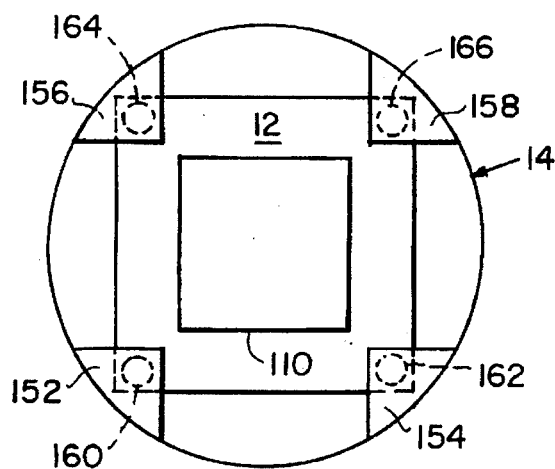
FIG. 11 is a schematic top plan view of the plate holder and plate of FIG. 10.

Plate holder 14 is shown in more detail in FIGS. 10 and 11. Rotation of plate 12 is accomplished by placing it within plate inspection cavity 151 of plate holder 14 on rotation spindle 108. Plate holder 14 accommodates multiple plate sizes and thicknesses. Plate 12 is pressed laterally against precision reference surfaces 152, 154, 156 and 158 by spring loaded plungers 160, 162, 164 and 166. This provides accurate and stable positioning of plate 12 both axially and radially with respect to rotation spindle 108 during inspection.

Figure 12:
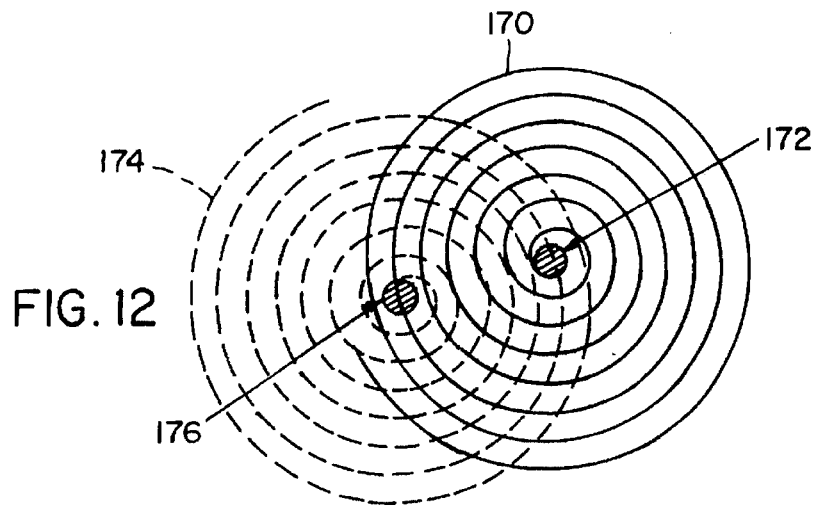
FIG. 12 is a schematic top plan view of two spiral beam path traces on a plate under inspection with the plate located in two translationally displaced positions.

Although the system according to this invention is capable of loading plate 12 and positioning it such that its center is within approximately 10-50 micrometers from the center of rotation of plate holder 14 and beam 34 is focussed very close to the center of the plate holder 14, during inspection any slight error in positioning causes a blind spot of inspection proximate the center point. In order to obviate this problem, plate 12 is inspected at least twice beginning at different inspection starting points. Plate 12 is first inspected with an initial inspection starting point such that beam path 170, FIG. 12, is achieved. Beam path 170, however, leaves a blind spot 172 on the surface of plate 12 (not shown in this view), which is not inspected. Thus, inspection is repeated after a slight repositioning or offset of plate 12 within plate holder 14. After plate repositioning, a second beam path 174 is traced on the surface of plate 12 which has a blind spot 176. It can be seen that by instituting multiple traces on the surface of plate 12 the blind spot 172 and 176 of each beam path 170 and 174 is inspected by the other beam path. Plate 12 is typically off-set approximately 50 to 200 micrometers from the first inspection to the second inspection so that blind spot 176 of second inspection beam path 174 does not positively coincide with blind spot 172 of first inspection beam path 170. The offsetting can be achieved by simply releasing and regripping plate 12 while permitting gravity to shift plate 12 within the tolerance of plate holder 14.

Figure 13B:
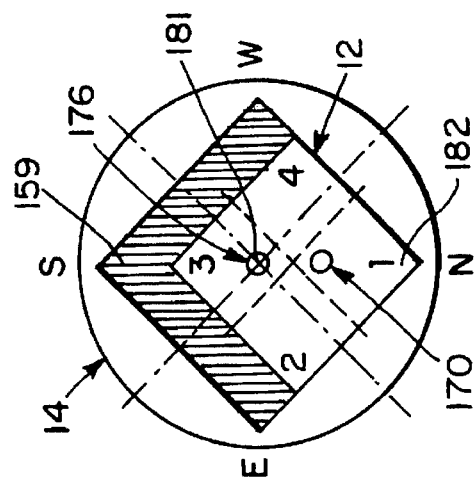
FIG. 13B is a view of the plate holder of FIG. 13A with a plate mounted therein proximate the south side of the plate inspection cavity for initial plate inspection.
Figure 13D:
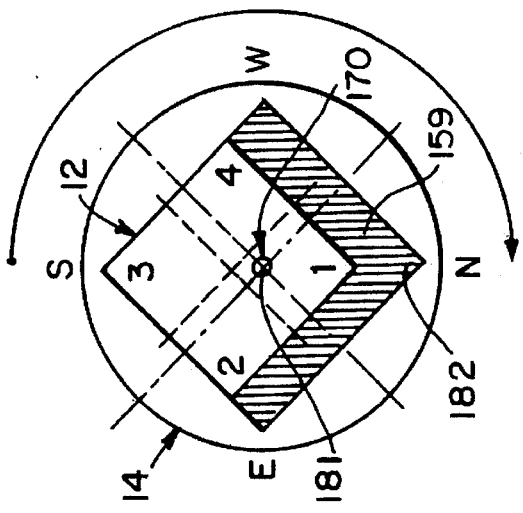
FIG. 13D is a view similar to FIGS. 13B and 13C but with the plate mounted proximate the north portion of the plate inspection cavity so that the plate may be reinspected.
Figure 13A:
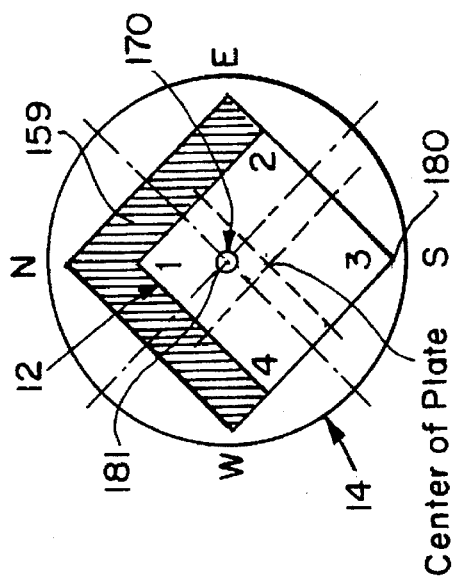
FIG. 13A is a schematic top plan view of the plate holder shown in FIGS. 1, 10 and 11 according to this invention without a plate loaded therein.
Figure 13C:
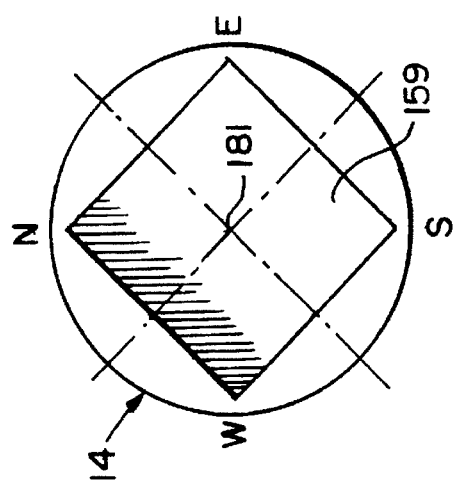
FIG. 13C depicts the plate holder rotated 180° from its position in FIG. 13B.

The reloading and reinspection process is depicted in FIGS. 13A-D. Plate holder 14, FIG. 13A, is shown without plate 12 loaded within plate inspection cavity 159. In FIG. 13B plate 12 is loaded in plate inspection cavity 159 at the south corner 180 of plate inspection cavity 159. Inspection of plate 12 is undertaken beginning proximate the center of rotation 181 of plate holder 14 and when completed a blind spot of inspection 170 is present which is aligned with the center of rotation of plate holder 14. Since plate 12 is loaded against south corner 180 of cavity 159 instead of being loaded with its center in alignment with the center of rotation 181, blind spot 170 is not aligned with the center of plate 12. In FIG. 13C plate holder 14 is rotated 180° so that its north corner 182 is now located in the same position as the south corner 180 is located in FIG. 14B. As noted above, plate holder 14 is positioned vertically, therefore, when spring-loaded plungers 160, 162, 164 and 166 are released, plate 12 falls so that it is loaded to the north corner 182 of cavity 159 as is shown in FIG. 13D. Plate 12 is then re-inspected and a second blind spot 176 is formed again at the center of rotation of plate holder 14, but slightly off center of plate 12. As shown in FIG. 12, by reloading and reinspecting both blind spots 172 and 176 are in fact inspected.

Figure 9:
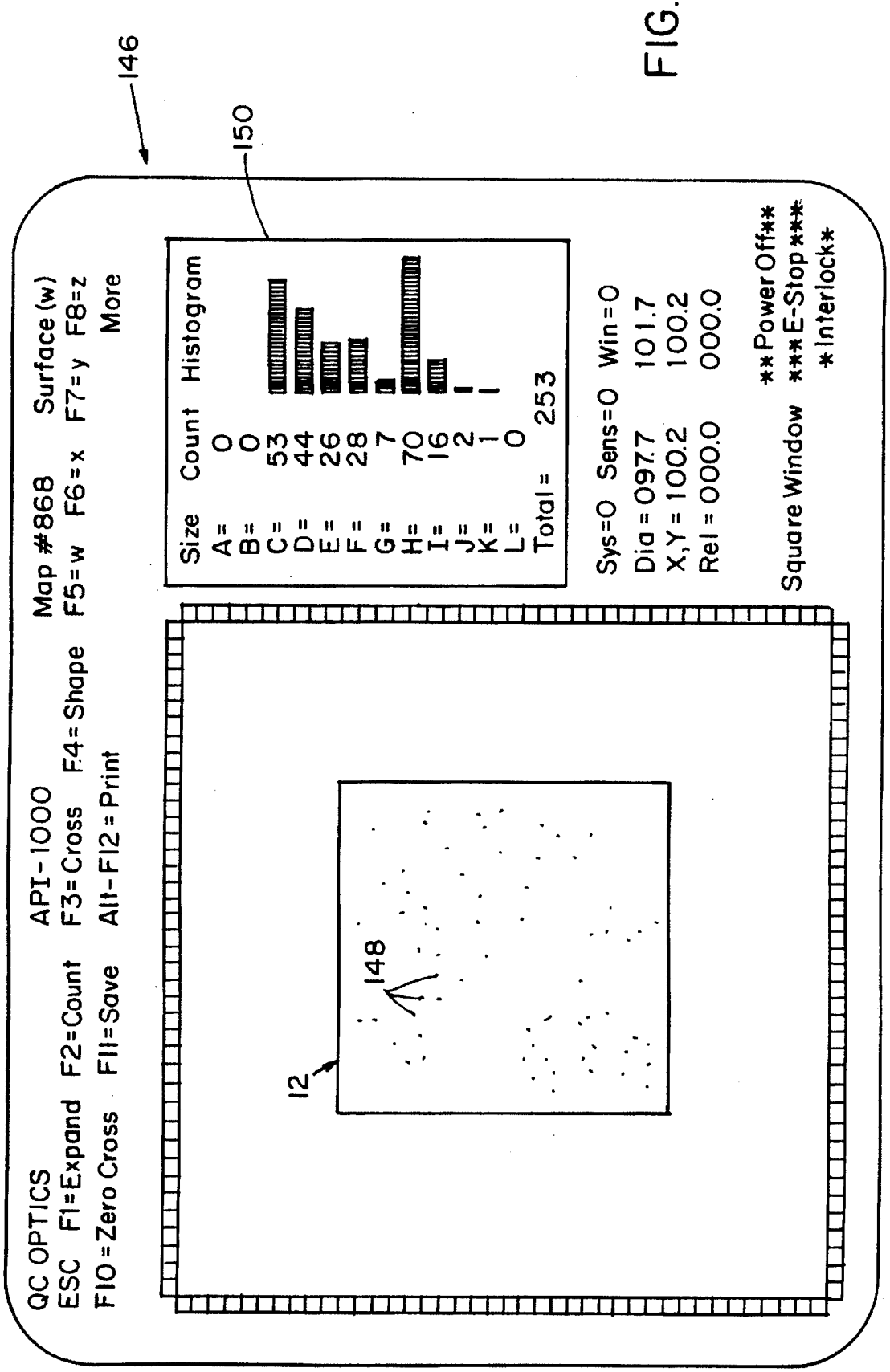
FIG. 9 is a detailed view of an image showing locations of the detected flaws produced on the display of FIG. 8.
Figure 14:
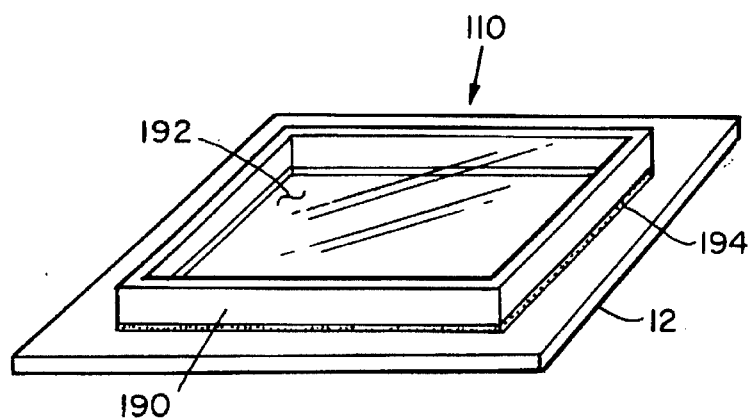
FIG. 14 is a diagrammatic three-dimensional view showing a pellicle covering a portion of a plate.
Figure 15:
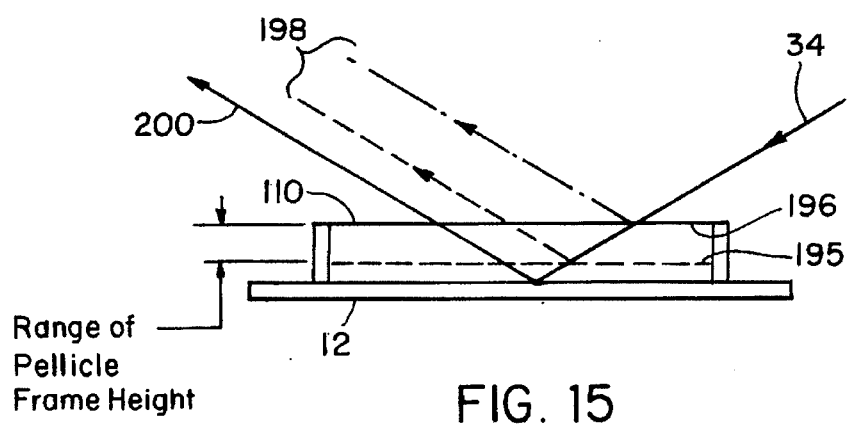
FIG. 15 is a cross-sectional view of the pellicle of FIG. 14 depicting the ultraviolet laser light reflected by the pellicle surface.

Pellicle 110 is shown in detail in FIG. 14 to include pellicle frame 190 which is typically made of aluminum and is 2-10 millimeters high and 1-3 millimeters wide. Pellicle film 192 which is approximately 0.8-3 micrometers thick is tightly stretched over pellicle frame 190 and both the frame and film are adhered to plate 12 by an adhesive layer 194. Pellicle 110, FIG. 16, diverts light by reflecting a portion of illuminating convergence beam 34 as indicated by reflected light 198. The range of position of reflected light 198 shown is due to the possibility of differing heights of pellicle 110 from a low height shown at 195 of approximately 2 millimeters to the approximately 10 millimeter maximum height shown at 196. The light reflected from plate 12, shown at beam 200, is collected by reflectometer detector 48 and, as shown in FIG. 9, used to adjust the laser power to compensate for attenuation of light by pellicle 110 which would otherwise be delivered to the surface of plate 12 and subsequently to detectors 38 and 40. As described above, the laser power may be increased to compensate for this lost illumination intensity. In the alternative the detectors' sensitivity or the detector calibration curve may be modified to account for the illumination lost due to the diverting action of pellicle 110.

Figure 16:
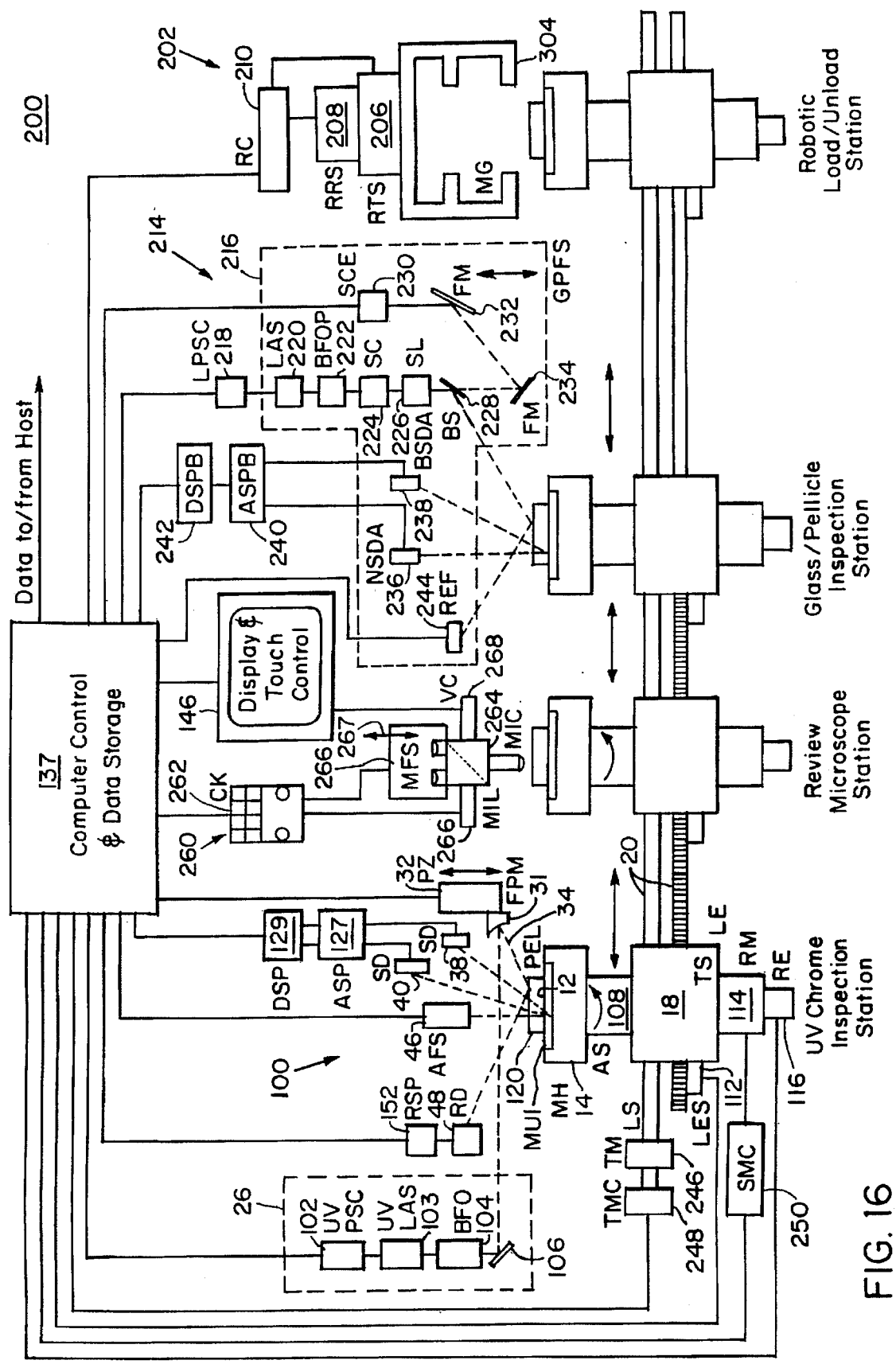
FIG. 16 is a functional block diagram of an inspection system incorporating the inspection station of FIG. 8.

There is shown in FIG. 16 inspection station 100 according to this invention as a component in plate inspection system 200. The first station in system 200 is robotic load/unload station 202 which includes plate gripper 204 for gripping plate 12 and placing it within plate holder 14 for inspection by system 200. Plate gripper 204 is also used to remove plate 12 after inspection of its primary chrome patterned surface is complete and to place plate 12 within plate holder 108 in an inverted position for inspection of its opposite non-patterned surface. Plate gripper 204 is positioned by robot translation stage 206 and robot rotation stage 208 which are under the control of robot controller 210. Computer control and data storage unit 137 drives robot controller 210.

The second station within system 200 is glass/pellicle inspection station 214 which is used to inspect the surface of pellicle 110 and it may be used to inspect the second non-patterned surface of plate 12 which does not require very accurate detection. This station is configured in the same manner as the device disclosed in U.S. Pat. No. 4,943,734, discussed in the Background of Invention, and which is available as the API-3000 sold by the assignee of the instant application, QC Optics, Inc., Burlington, Mass. Station 214 includes focusing stage 216 which under control of blue laser power supply and control 218 drives blue laser 220 to output a blue laser beam which is supplied to beam focusing optics 222, scanner 224, scan lens 226, beam splitter 228 and eventually to the surface of pellicle 110 which is scanned. Scanning encoder 230 and blending mirrors 232 and 234 are scanned with the scanning beam and provide computer control and data storage unit 137 with the beam position.

Normal scattering detector array 236 and back scattering detector array 238 provide electrical signals indicative of the normal and back scattered light scattered from the surface of pellicle 110 or the non-patterned surface of plate 12 to analog signal processor 240, digital signal processor 242, and ultimately to computer control and data storage unit 137. The signal from the normal scattering detector array 236 is used to position focusing stage 216 to focus the beam from beam splitter 228 onto the surface of pellicle 110 or onto the non-patterned surface of plate 12. When scanning pellicle 110, back scattering detector array 238 is used to detect high intensity back scattered energy encountered when the beam illuminates the aluminum frame of the pellicle. The location of each position of the pellicle frame is stored and mapped in computer control and data storage unit 137. This pellicle frame map is used when plate 12 is translated to inspection station 100 to undergo inspection according to this invention as described above. At inspection station 100, when plate 12 is inspected, inspection data is automatically discarded at the locations where the pellicle frame is present and outside of the pellicle frame. Thus, the pellicle frame and areas outside of the pellicle frame are essentially masked out of the inspection process. This is very useful in that the pellicle frame and the areas outside of the pellicle frame, upon inspection, provide unnecessary information which would otherwise overload detectors 38 and 40 and the system memory.

Inspection station 214 also includes a reflectance detector 244 which is used to detect the amount of light reflected from the pellicle to provide a signal to computer control and data storage circuit 137 to adjust the laser output to compensate for the attenuated signal by the pellicle.

After the pellicle is inspected at glass/pellicle inspection station 214, plate 12 is translated to inspection station 100 where the plate is inspected as described above. The translation of plate holder 14 is achieved by translation motor 246 under the control of translation motor controller 248 which is driven by computer control and data storage unit 137. The rotation of plate holder 14 is achieved by rotation motor 114 under the control of rotation motor controller 250 which is also driven by computer control and data storage unit 137.

The final station in system 200 is microscope review station 260 which an operator may utilize to visually inspect the detected flaws. Station 260 includes a control keypad 262 which allows the operator to control the review process. The operator may review successive particles on display 146, change the illumination brightness and/or label each particle detected, among other things. Review microscope 264 includes microscope illuminator 266 and video camera 268 which supplies display 146 with a video image of the surface of plate 12. Microscope focusing stage 266 translates microscope 264 in the direction of arrows 267 by control key/pad and 262.

Figure 17:
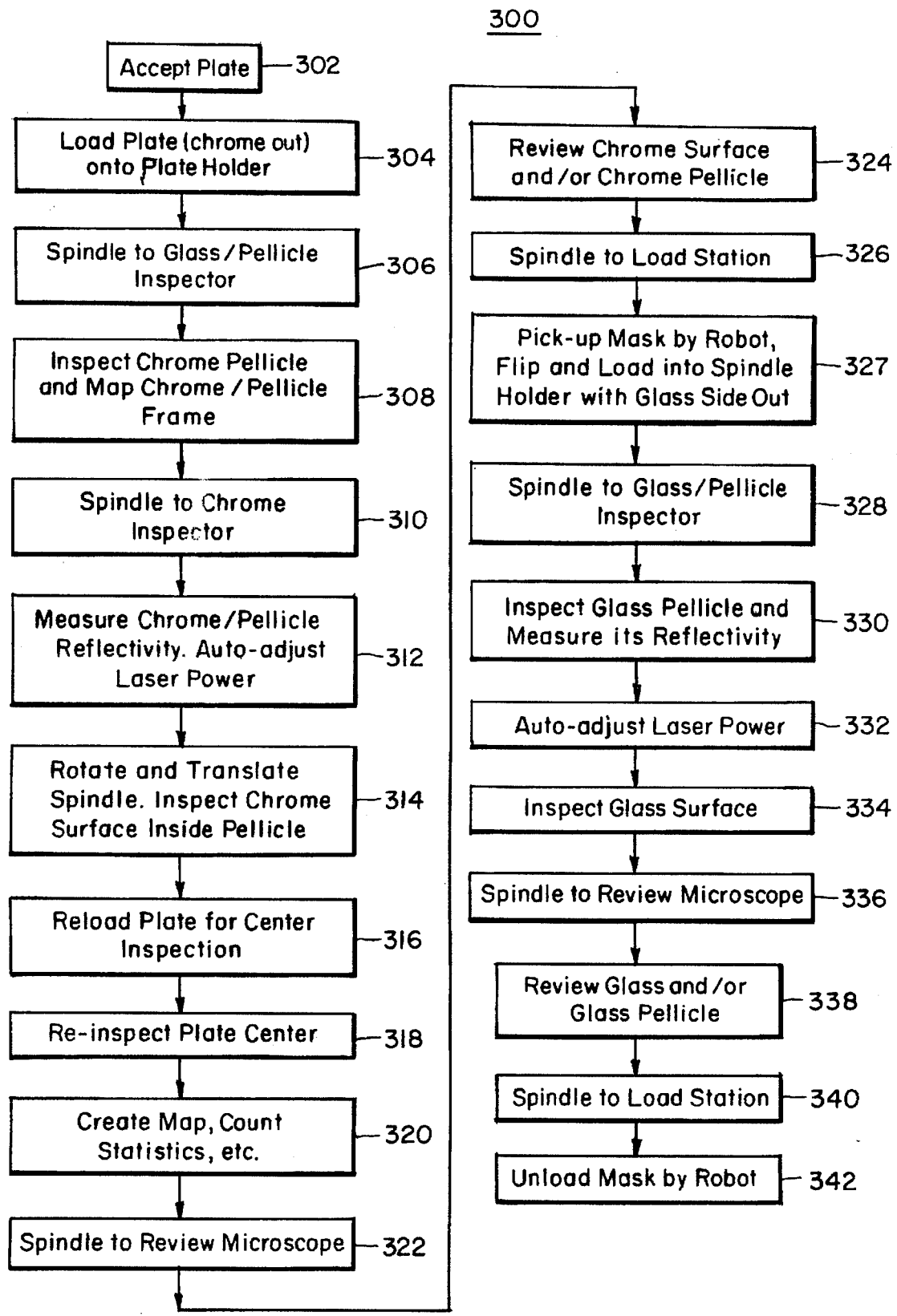
FIG. 17 is a flow chart depicting the software steps carried out in the computer control and data storage unit of FIG. 16.

Flow chart 300, FIG. 17, delineates the software steps accomplished in computer control and data storage unit 137 for the inspection of a plate. In step 302 a plate is accepted by plate gripper 204, FIG. 16, and at step 304 the plate is loaded onto plate holder 14. Plate holder 14 is then translated to glass/pellicle inspection station 214 at step 306 and at step 308 the pellicle is inspected and the pellicle frame locations (positions) are mapped. At step 310 plate holder 14 is translated to inspection station 100. At step 312 the pellicle reflectivity is measured and the laser power is compensated to adjust for the illumination energy attenuated by the pellicle. At step 314 plate 12 is rotated and translated until a first beam path (e.g. 170, FIG. 12) is traced and inspection of the surface of plate 12, excluding the portions covered by the pellicle frame and outside the pellicle frame, is completed. At step 316 plate 12 is reloaded, as described above with regard to FIGS. 12 and 13, and at step 318 the center of the plate is reinspected. At step 320 a map of the flaw locations on the surface of plate 12 is created and stored within a computer control and data storage unit 137 and/or displayed on display 146. At step 322 the plate holder 14 and plate 12 are translated to microscope review stage 260 where at step 324, the surface of plate 12 and/or of chrome side pellicle may be visually reviewed by the operator. At step 326 plate holder 14 and plate 12 are translated to load/unload station 202 when at step 326 the plate 12 is unloaded and reloaded with its second, non-patterned surface (glass side) facing up so it can be inspected. At step 328 plate 12 with its glass surface face up is translated to glass/pellicle inspector 214. At step 330 the pellicle covering the glass surface of plate 12 is inspected and its reflectivity is obtained. The laser power of glass/pellicle inspection station 214 is adjusted at step 332 to compensate for the attenuated illumination energy due to the pellicle and at step 334 the glass surface is inspected by glass/pellicle inspection station 214. Since the inspection of the underside surface of plate 12 need not be as accurately inspected, inspection can be performed at glass/pellicle inspection station 214. At step 336 plate 12 is translated to microscope review station 260 and at step 338 the glass surface of plate 12 and/or glass side pellicle are inspected under microscope 264. At step 340 plate 12 and plate holder 14 are translated to robotic load/unload station 202 and plate 12 is unloaded by plate gripper 204 at step 342.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. An improved optical inspection system for detecting flaws on a diffractive surface containing surface patterns, comprising:
   an ultraviolet illumination means for illuminating a region on the diffractive surface with a stationary ultraviolet beam to generate a scattered intensity distribution in response to either a flaw or a surface pattern;
   means for detecting the intensity level of said scattered intensity distribution at a plurality of locations about the diffractive surface;
   means, responsive to said means for detecting, for establishing a minimum detected intensity level;
   means, responsive to said minimum detected intensity level, for indicating the absence of a flaw on the illuminated region of the diffractive surface when said minimum detected intensity level is below a threshold intensity level and for indicating the presence of a flaw on the illuminated region of the diffractive surface when said minimum detected intensity level exceeds said threshold intensity level; and
   means for moving the diffractive surface to generate a scan pattern on the diffractive surface to inspect the surface;
   said means for moving includes means for positioning the diffractive surface in a first position with respect to said ultraviolet illumination means for conducting a first inspection of the diffractive surface and for positioning the diffractive surface in a second position with respect to said ultraviolet illumination means for conducting a second inspection of the diffractive surface to insure full inspection of the surface.

2. The improved optical inspection system of claim 1 in which said ultraviolet illumination means includes an ultraviolet laser which provides an ultraviolet laser beam for illuminating the diffractive surface.

3. The improved optical inspection system of claim 2 in which said ultraviolet laser is a stationary ultraviolet laser.

4. The improved optical inspection system of claim 2 in which said ultraviolet laser projects an elliptical beam spot on the diffractive surface.

5. The improved optical inspection system of claim 2 in which said ultraviolet laser beam impinges on the diffractive surface at an angle of approximately 60° from normal to the surface.

6. The improved optical inspection system of claim 2 in which said means for moving includes means for rotating and translating the diffractive surface to establish a spiral trace including a plurality of revolutions of said ultraviolet laser beam on the diffractive surface.

7. The improved optical inspection system of claim 6 in which the beam width is at least as large as the beam trace pitch to ensure inspection of the regions between revolutions of the trace.

8. The improved optical inspection system of claim 7 in which said beam trace pitch is no greater than approximately 3 micrometers.

9. The improved optical inspection system of claim 1 in which said means for illuminating includes reflective means for directing and focusing the illumination on the diffractive surface.

10. The improved optical inspection system of claim 9 in which said reflective means includes a mirror.

11. The improved optical inspection system of claim 10 in which said mirror is an off-axis parabolic mirror.

12. The improved optical inspection system of claim 1 in which said means for detecting includes a first detector at a first location proximate the diffractive surface for detecting the intensity level of said scattered intensity distribution at said first location and a second detector at a second location proximate the diffractive surface for detecting the intensity level of said scattered intensity distribution at said second location.

13. The improved optical inspection system of claim 1 in which said means for detecting are positioned at locations about the diffractive surface where the intensity level of the scattered intensity distribution from the surface pattern is expected to be below said threshold intensity level.

14. The improved optical inspection system of claim 1 further including means, responsive to said minimum detected intensity level, for determining flaw size.

15. The improved optical inspection system of claim 14 in which said means for moving includes encoder means for determining the position of the illuminated region on the diffractive surface.

16. The improved optical inspection system of claim 15 further including means, responsive to said means for indicating and said means for determining the position of the illuminated region, for storing the locations of the flaws detected.

17. The improved optical inspection system of claim 16 further including means for determining the regions on the diffractive surface covered by a pellicle frame and the regions on the diffractive surface external of said pellicle frame.

18. The improved optical inspection system of claim 17 further including means, responsive to said means for determining the regions on the diffractive surface covered by the pellicle frame and the regions on the diffractive surface external of said pellicle frame, for discarding information from said means for detecting at said regions on the diffractive surface.

19. The improved optical inspection system of claim 15 further including means, responsive to said means for determining flaw size and said means for determining the position of the illuminated region on the surface, for storing the location and size of the flaws detected.

20. The improved optical inspection system of claim 19 further including means for displaying the locations of the flaws detected.

21. An improved optical inspection method for detecting flaws on a diffractive surface containing surface patterns, comprising:
   illuminating a region on the diffractive surface with ultraviolet illumination to generate a scattered intensity distribution in response to either a flaw or a surface pattern, said ultraviolet illuminating said region with a stationary ultraviolet beam;

detecting the intensity level of said scattered intensity distribution at a plurality of locations about the diffractive surface;

establishing a minimum detected intensity level;

indicating the absence of a flaw on the illuminated region of the diffractive surface when said minimum detected intensity level is below a threshold level and the presence of a flaw on the illuminated region of the diffractive surface when said minimum detected intensity level exceeds said threshold intensity level;

positioning the diffractive surface in a first position with respect to said ultraviolet illumination;

moving the diffractive surface to generate a first scan pattern on the diffractive surface;

positioning the diffractive surface in a second position with respect to said ultraviolet illumination; and moving the diffractive surface to generate a second scan pattern on the diffractive surface to insure full inspection of the surface.

22. The improved optical inspection method of claim 21 in which the step of illuminating includes providing an ultraviolet laser beam to the diffractive surface.

23. The improved optical inspection method of claim 22 in which the step of providing an ultraviolet laser beam includes providing a stationary ultraviolet laser beam.

24. The improved optical inspection method of claim 22 in which the step of providing an ultraviolet laser beam includes projecting an elliptical beam spot onto the diffractive surface.

25. The improved optical inspection method of claim 22 in which the step of providing an ultraviolet laser beam includes directing the ultraviolet laser beam to the surface at an angle of approximately 60° from normal to the surface.

26. The improved optical inspection method of claim 22 in which the step of moving includes rotating and translating the diffractive surface to establish a spiral trace with a plurality of revolutions of said ultraviolet laser beam on the diffractive surface.

27. The improved optical inspection method of claim 26 in which the step of rotating and translating includes overlapping each said revolution of said spiral trace with adjacent revolutions to insure inspection of the regions between each revolution.

28. The improved optical inspection method of claim 26 in which the step of rotating and translating includes spacing said revolutions no greater than approximately 3 micrometers apart.

29. The improved optical inspection method of claim 21 in which the step of detecting includes detecting the intensity level of said scattered intensity distribution at a first location proximate the diffractive surface and detecting the intensity level of said scattered intensity distribution at a second location proximate the diffractive surface.

30. The improved optical inspection method of claim 21 in which the step of detecting includes detecting the intensity level of said scattered intensity distribution at locations about the diffractive surface where the intensity level of the scattered intensity distribution from the surface pattern is expected to be below said threshold intensity level.

31. The improved optical inspection method of claim 21 further including determining flaw size.

32. The improved optical inspection method of claim 31 in which the step of moving includes determining the position of the illuminated region on the diffractive surface.

33. The improved optical inspection method of claim 32 further including storing the locations of the flaws detected.

34. The improved optical inspection method of claim 33 further including displaying the locations of the flaws detected.

35. The improved optical inspection method of claim 33 further including determining the regions on the diffractive surface covered by a pellicle frame and the regions on the diffractive surface external of said pellicle frame.

36. The improved optical inspection method of claim 35 in which the step of determining the regions on the diffractive surface covered by the pellicle frame and the regions on the diffractive surface external of said pellicle frame includes discarding detected intensity levels from said regions on the diffractive surface.

37. The improved optical inspection method of claim 32 further including storing the locations and sizes of the flaws detected.

38. An improved optical inspection system for detecting flaws on a diffractive surface containing surface patterns, comprising:

an ultraviolet illumination means for illuminating a region on the diffractive surface to generate a scattered intensity distribution in response to either a flaw or a surface pattern;

means for detecting the intensity level of said scattered intensity distribution at a plurality of locations about the diffractive surface;

means, responsive to said means for detecting, for establishing a minimum detected intensity level;

means, responsive to said minimum detected intensity level, for indicating the absence of a flaw on the illuminated region of the diffractive surface when said minimum detected intensity level is below a threshold intensity level and for indicating the presence of a flaw on the illuminated region of the diffractive surface when said minimum detected intensity level exceeds said threshold intensity level;

means for moving the diffractive surface to generate a scan pattern on the diffractive surface to inspect the diffractive surface; and means for determining the regions on the diffractive surface covered by a pellicle frame and the regions on the diffractive surface external of said pellicle frame.

39. The improved optical inspection system of claim 38 further including means, responsive to said means for determining the regions on the diffractive surface covered by the pellicle frame and the regions on the diffractive surface external of said pellicle frame, for discarding information from said means for detecting at said regions on the diffractive surface.

40. An improved optical inspection method for detecting flaws on a diffractive surface containing surface patterns, comprising:

illuminating a region on the diffractive surface with ultraviolet illumination to generate a scattered intensity distribution in response to either a flaw or a surface pattern;

detecting the intensity level of said scattered intensity distribution at a plurality of locations about the diffractive surface;

establishing a minimum detected intensity level;

indicating the absence of a flaw on the illuminated region of the diffractive surface when said minimum detected intensity level is below a threshold level and the presence a flaw on the illuminated region of the diffractive surface when said minimum detected intensity level exceeds said threshold intensity level;

moving the diffractive surface to generate a scan pattern on the diffractive surface to inspect the diffractive surface; and determining the regions on the diffractive surface covered by a pellicle frame and the regions on the diffractive surface external of said pellicle frame.

41. The improved optical inspection method of claim 40 in which the step of determining the regions on the diffractive surface covered by the pellicle frame and the regions on the diffractive surface external of said pellicle frame includes discarding detected intensity levels from said regions on the diffractive surface.

* * * * *